United States Patent [19]

Binder et al.

[11] 4,029,563

[45] June 14, 1977

[54] ELECTROCHEMICAL MEASURING CELL

[75] Inventors: Horst Binder, Karben-Petterweil; Reinhard Knödler, Hofheim; Alfons Köhling, Eschborn; Gerd Sandstede, Frankfurt am Main, all of Germany

[73] Assignee: Dragerwerk Aktiengesellschaft, Germany

[22] Filed: Dec. 2, 1974

[21] Appl. No.: 529,007

[52] U.S. Cl. .................. 204/195 R; 204/1 T
[51] Int. Cl.² ................ G01N 27/46; G01N 27/52
[58] Field of Search ............ 204/1 F, 1 T, 1 Y, 1 P, 204/195 P, 195 R

[56] References Cited

UNITED STATES PATENTS

| 2,117,596 | 5/1938 | Bender et al. | 204/195 G |
| 2,861,926 | 11/1958 | Jacobson | 204/1 Y |
| 3,493,484 | 2/1970 | Berg et al. | 204/195 R |
| 3,622,488 | 11/1971 | Chand et al. | 204/195 P |
| 3,756,923 | 9/1973 | Dahms | 204/1 F |
| 3,776,832 | 12/1973 | Oswin et al. | 204/195 R |
| 3,795,589 | 3/1974 | Dahms | 204/1 T |
| 3,803,006 | 4/1974 | Krueger et al. | 204/1 F |

FOREIGN PATENTS OR APPLICATIONS 1,233,173 1/1967 Germany .................. 204/195 R Primary Examiner—G. L. Kaplan
Attorney, Agent, or Firm—McGlew and Tuttle

[57] ABSTRACT

An electrochemical measuring cell for the continuous measurement of sulfur dioxide content of the air in emission and immission areas, comprises a cell housing which has a test gas cell chamber therein for the connection for circulating the gas to be tested into the chamber. The chamber also contains a diffusion electrode which serves as an anode and which is made up of a reversible organic redox system. The cathode comprises an active mass having a redox potential higher than the redox potential of the anode. An immobilized electrolyte is disposed between the anode and the cathode and the anode and cathode are connected to a device for measuring the short circuit current. The diffusion electrode is manufactured from a mixture of chloranil and sodium tungsten bronze which is pulverized in a ball mill for sixteen hours and mixed with a polyethylene powder and sodium sulfate and is then compressed. The cathode is made of a manganese dioxide which is intimately mixed with graphited coal as the conductive additive. The immobilized electrolyte is made of an asbestos fiber and phosphoric acid paste.

3 Claims, 1 Drawing Figure

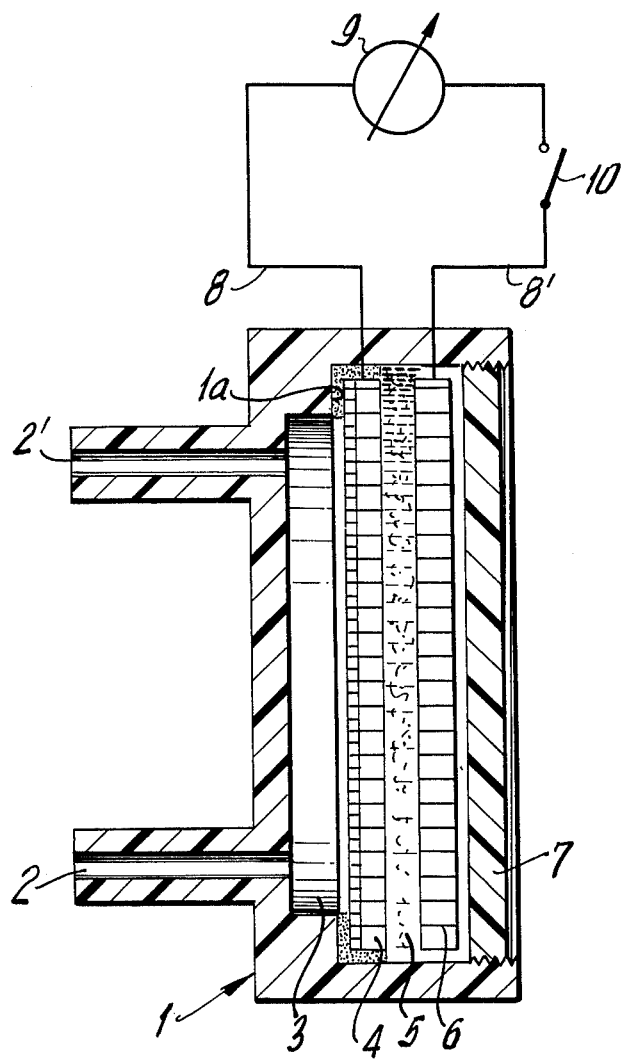

ELECTROCHEMICAL MEASURING CELL

FIELD AND BACKGROUND OF THE INVENTION

This invention relates in general to the construction of devices for measuring contaminants in gases, such as air, and, in particular, to a new and useful electrochemical measuring cell for the continuous measurement of the sulfur dioxide content in the air in emission as well as imission areas.

DESCRIPTION OF THE PRIOR ART

One of the most widespread air pollutants is sulfur dioxide since it is produced during the combustion of most fuels and in many other technological processes and so that it belongs to the most representative of air pollutants. Depending upon the manner in which the sulfur dioxide is produced, it appears along with various gaseous, liquid and solid substances, and serves as an indicator for the general air quality. Thus, a high $SO_2$ concentration is a distinct warning signal indicating that other compounds may also be present in higher concentration. Noxious effects to be taken seriously can be observed at considerably low concentrations, such as, for example, at an average concentration of 300 $\mu g/m^3$ through 3 to 4 days as mentioned in "Air Quality Criteria for Sulfur Dioxides", National Air Pollution Control Administration, Publication No. AP 50, Washington, 1969.

There are many known methods and measuring instruments for the continuous measurement of the $SO_2$ concentration. For example, the VDI Manual "Reinhaltung der Luft" (Keeping the Air Clean), Measuring of the Sulfur Dioxide Concentration (VDI 2451), Dusseldorf. Aside from the photometric ones, the gas analyzers using the conductivity method have proved to be particularly sensitive as indicators. The instruments work on a chemophysical principle of measurement. They measure the conductivity of a reactive solution prior to, and after its reaction with sulfur dioxide.

A known analyzer which permits the continuous measurement of extremely small $SO_2$ concentrations is based on the principle of a continuous coulometric titration. H. J. Brower, et al (Philips Technische Rundschau, 32 (1971/72), page 29), describes a device in which, in a flow process, the measured air is brought into intimate contact with a solution containing a bromide, in which the quantity of bromide necessary for a quantitative reaction is produced. The current needed, therefore, serves as a measure of the $SO_2$ concentration in the air. Such analyzers have been used for establishing a network of measuring points for measuring the air pollution in the estuary area of the Rhine.

The extreme noxiousness of $SO_2$ makes it necessary, aside from the provision of a large network of measuring stations registering the immision, to limit the $SO_2$ emission, that is, to control all of the $SO_2$ emitters, such as, industrial plants, power plants, refuse incineration plants, etc. Such plants are controlled in respect to the observation of the emission limit values in order to check the anti-pollution installations for their permanent efficiency and to determine the range of influence of extraordinary emission sources which may appear, for example, due to operational troubles or improper operation or negligence in service. For such a control, the known apparatus and measuring methods are usable only within limits, and there is a need for a portable device which would make it possible to carry out the necessary measurements at any time and at any place.

SUMMARY OF THE INVENTION

The present invention provides a handy, reliable, and easily operable device for the continuous measurement and control of the sulfur dioxide content in the air. In accordance with the invention, there is provided an electrochemical measuring cell which has characteristics such that the short circuit potential across the anode and cathode thereof will give an indication of the $SO_2$ content in a gas. The cell may be simply constructed with relatively small manufacturing costs and it may be sufficiently small so that it may be easily manipulated and operated even by unskilled persons. In addition, the device is so small and handy that it may be moved from place to place. The inventive measuring cell is constructed without any movable parts or parts which are exposed to wear and, therefore, in practice, may operate for long periods substantially without any maintenance. Further, the device is extremely reliable and safe in operation, and this is particularly important for long term emission controls. Moreover, for continuous operation, it is advantageous that no power supply is needed, except for perhaps connecting the device to another warning or registering device, or the like.

The measuring cell, constructed in accordance with the invention, comprises a diffusion electrode and an unpolarizable cathode in an acid electrolyte. As a rule, the complete arrangement is placed in a plastic housing. The two electrodes are short-circuited through a sensitive micro-ammeter. The measuring cell is sensitive enough to be able to measure the $SO_2$ concentrations within the immission area and within an emission area also.

The diffusion electrode of the inventive measuring cell includes a hydrophobic back or interior layer in a cell and gas chamber into which the air may be delivered for testing purposes. It also includes a hydrophilic active layer which is in direct contact with the electrolyte and comprises a fully reversible, organic redox system, preferably, of quinoid structure. As soon as air to be examined passes into the interior chamber of the housing of the diffusion electrode, the $SO_2$ contained therein penetrates through the diffusion layer of this electrode to the active layer and insofar as this layer comprises an organic redox system, having a quinoid structure, it reduces the quinone to the corresponding hydroquinone. The hydroquinone is oxidized to quinone again and releases electrons which are accepted by the unpolarized cathode. The same applies analogously to diffusion electrodes comprising other reversible organic oxidation reduction systems.

The current necessary for the transformation flows through the micro-ammeter to the unpolarizable cathode and can be evaluated as a measure of the $SO_2$ concentration in the air. Of all the noxious substances contained in the air, only hydrogen sulfide also reduces the quinone to the hydroquinone and thereby may affect the result of the measurement. Since, however, the hydrogen sulfide content is generally smaller by far than the $SO_2$ content, this interfering sensitivity can be neglected. By any of the other reducing noxious substances, such as carbon monoxide, the measurements are not adulterated.

In an advantageous development of the invention, the redox system used for the diffusion electrode comprises substituted p-benzoquinones, O-benzoquinones or diphenoquinones with F, Cl, CH$_3$, SO$_3$H or CN as substituents. In such a case, tetrachlor-p-benzoquinone or tetramethyl-p-benzoquinone have proved to be particularly suitable.

Since all of the above-mentioned quinones are nonconductors, they must be mixed before using them for the inventive diffusion electrode with conductive substances. Suitable conductive additives are compounds which are stable in acid electrolytes and do not react themselves with the SO$_2$, nor with another substance contained in the air. In addition, their surface should be small and not porous so as to permit a quick exchange of gas and to prevent a delay of the SO$_2$ indication response caused by an SO$_2$ content in the pores of these compounds. Suitable additives are graphite and tungsten bronzes, for example.

The mixture of quinone and a conductive substance may be molded or sintered with a thermoplastic, such as polyethylene, with or without addition of a pore-forming material, to a mechanically resistant electrode.

The substances usable as the active mass for the unpolarizable cathode must have a higher oxidation potential than the quinones in the diffusion electrode and, under high current density, they must be electrochemically reducible without disturbing losses of their potential. It has been found that particularly suitable substances in this respect are oxides and/or mixed oxides of the transition metals and, especially, manganates and/or cobaltates. At the oxidation of the hydroquinone, these substances accept the released electrons. If for example, MnO$_2$ is used, it is reduced to bivalent manganese ion according to the equation:

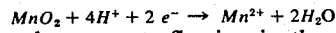
$$MnO_2 + 4H^+ + 2 e^- \rightarrow Mn^{2+} + 2H_2O$$

Since the currents flowing in the measuring cell are very small, the needed quantity of oxides can be deposited in the measuring cell for long periods of operation.

Due to the short-circuit between the two electrodes in the cell though the micro-ammeter, the potential of the cathode is also applied to the diffusion electrode serving as an anode. At this potential, the entire quantity of hydroquinone formed by the reduction with SO$_2$ is instantly and completely reoxidized to quinone.

Any strong acid, such as perchloric acid, sulfuric acid or phosphoric acid may be used as an electrolyte. A moderately concentrated phosphoric acid has proved to be a very suitable electrolyte since, in this case, the water absorption and release through the diffusion layer is minimized. Because, in accordance with the invention, the acid electrolyte is immobilized, for example, by absorption is asbestos fibers or in a alumina, the measuring cell can be operated in any position in contrast to the cells with free electrolytes. The diffusion electrode for the inventive cell is manufactured from a mixture of chloranil and pulverized sodium tungsten bronze which is also mixed with a polyethylene powder and sodium sulfate and compressed in a mold. The cathode is made of manganese dioxide which is mixed with graphited coal as the conductive additive.

Accordingly, it is an object of the invention to provide am improved device for measuring the sulfur dioxide content of a gas, such as air, which comprises a housing, having a chamber for the measuring cell, and into which the gas to be tested may be placed and which includes, a reversible, organic redox system forming an anode and a cathode made up of an active mass having redox potential higher than the anode with an immobilized electrolyte therebetween and with the electrodes connected to a short-circuit current measuring device.

A further object of the invention is to provide a method of making an electrochemical measuring cell and the anode and cathode therefor.

A further object of the invention is to provide a device for measuring sulfur dioxide content in gases which is simple in design, rugged in construction, and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

BRIEF DESCRIPTION OF THE DRAWING

The only FIGURE of the drawing comprises a cross-sectional view of an electrochemical measuring cell, constructed in accordance with the invention.

DESCRIPTION OF THE PREFERRED EMBODIMENT

Referring to the drawing in particular, the invention embodied therein comprises an electrochemical measuring device for measuring the SO$_2$ content in gases, such as air, and which comprises a housing, generally designated 1, having an interior gas and cell chamber 3, which is communicable with gas inlet and outlet connections and 2 and 2' for the passage of a gas to be tested therethrough. Housing 1 is made of an electrically non-conductive plastic material, for example, plexiglass.

In accordance with the invention a diffusion electrode 4 is arranged in spaced parallel relationship to a cathode 6 and an electrolyte 5 is positioned therebetween and sealed in one portion of the space 3. The electrolyte 5 is immobilized with a filling of asbestos fibers and the entire assembly is tightly positioned within space 3 and sealed at the outer open end of housing 1 by a threaded plate or closure disc 7. Plate 7 is also made of a non-conductive material, such as plexiglass. Contact wires 8 and 8' are connected to respective electrodes 4 and 6 and to respective terminals of a micro-ammeter 9. The contact wires 8 and 8' pass through openings in the housing which are sealed and fixed with an acid-resistant adhesive. In addition, the closing disc 7 is similarly sealed with such an adhesive, along with the opposite side of the cell at the outer end of the electrode 4.

The diffusion electrode 4 serves as an anode, and the diffusion electrode 6 comprises a cathode, and they are connected to each other through the micro-ammeter 9.

In order to put the inventive measuring cell into operation, it is only necessary to close a switch 10 in the connection to the micro-ammeter and this will produce a momentary high current flow raising the potential of the diffusion electrode 4 to the potential of the cathode 6. The inventive measuring cell is then ready for service and will indicate the SO$_2$ content of the air. This air may be circulated through the connection 2 and 2', for example, by a manual or electric pump, and the gas velocity should be sufficiently high so that a permanent supply of fresh air gas mixture is ensured. After amplification of the measuring signal corresponding to the current flow through the micro-ammeter 9, accurate determination of the $SO_2$ content of the air may be obtained. This determination may be connected to suitable recorders, printers or warning devices which are connected to the cell through the contact wires 8 and 8'. The apparatus may be calibrated in accordance with some of the methods described in the literature, for example, the publication, W. Breuer & K. Schreckling, ATM, Lfg 408 (January, 1970), V 723-34.

The diffusion electrode is manufactured from a mixture of chloranil and sodium tungsten bronze $Na_xWO_3$ with the portion $x$ from between 0.25 and 0.95. The sodium tungsten bronze is pulverized in a ball mill for sixteen hours. The combined chloranil and pulverized sodium tungsten bronze is mixed with polyethylene powder of a grain size of about 30 μm and sodium sulfate with a grain size of 25 to 60 μm in the volume ratio of 40:20:40. One gram of this mixture is filled into a mold having a diameter of 48 mm, and it is compressed at a pressure of 1 Mp/cm². Thereupon, the mold is opened at one side and a very small quantity of polyethylene powder is sprayed onto the blank still contained in the mold and a plate of porous polytetrafluoroethylene is placed thereon. The total is then pressed for one hour under presure of about 20 kp/cm² and at a temperature of 130° C. Thereby, the content is agglomerated to a stable electrode structure. Advantageously, a gold gauze is pressed in at the same time for the current tapping. The sodium sulfate serving as the pore-forming substance is eliminated by water. The electrode is hydrophobic to such an extent, that during the later operation, no electrolyte leaks out at the gas side.

In order to manufacture the cathode, manganese dioxide ($MnO_2$ is used as an active substance. 1000 mg of $MnO_2$ is mixed intimately with 400 mg of graphited coal as the conductive additive. 600 gm of polytetrafluoroethylene powder, having a grain size of 30 μm is then mixed with the first mixture, and this total mixture is suspended in about 20 ml of propanol and poured into a filtering flask having a diameter of 48 mm. Upon inserting a gold gauze, with a contact wire welded thereon into this muddy mass, the liquid is drained off and the remaining layer is dried for about one hour at 100° C. Subsequently, this layer is sintered for two hours under a moderate pressure of from 10 to 50 p/cm² at 370° C. A stable electrode is thereby obtained having a diameter of 48 mm and a porosity of about 50%.

The immobilized electrolyte is prepared by feeding asbestos fibers into a 15 $n$ phosphoric acid until a brushable paste is obtained. It is a simple matter to insert the two electrodes 4 and 6 into the space 3 and to seal the inner end at the location of a ledge 1a of housing 1 and to seal the opposite end by threading disc 7 onto this end and sealing it by suitable adhesive.

While a specific embodiment of the invention has been shown and described in detail to illustrate the application of the principles of the invention, it will be understood that the invention may be embodied otherwise without departing from such principles.

What is claimed is:

1. An electrochemical measuring cell for continuous measurement of the sulfur dioxide content of the air in emission and immission areas, comprising a cell having a test gas and cell chamber, a test gas connection for the passage of test gas into said test gas and cell chamber, a diffusion electrode serving as an anode and comprising a reversible, organic redox system located in said gas and test cell chamber, a cathode spaced from said anode and comprising an active mass having a redox potential higher than the redox potential of said anode, an immobilized electrolyte between said anode and said cathode, means connected between said anode and said cathode for measuring the short-circuit current therebetween; the redox system in the diffusion electrode having a quinoid structure and being present in a solid state.

2. An electrochemical measuring cell for continuous measurement of the sulfur dioxide content of the air in emission and immission areas, comprising a cell having a test gas and cell chamber, a test gas connection for the passage of test gas into said test gas and cell chamber, a diffusion electrode serving as an anode and comprising a reversible, organic redox system located in said gas and test cell chamber, a cathode spaced from said anode and comprising an active mass having a redox potential higher than the redox potential of said anode, an immobilized electrolyte between said anode and said cathode, means connected between said anode and said cathode for measuring the short-circuit current therebetween; said diffusion electrode as the redox system comprising substituted p-benzoquinones, O-benzoquinones or diphenoquinones with F, Cl, $CH_3$, $SO_3H$ or CN as substituents.

3. An electrochemical measuring cell for continuous measurement of the sulfur dioxide content of the air in emission or immission areas, comprising a cell having a test gas and cell chamber, a test gas connection for the passage of test gas into said test gas and cell chamber, a diffusion electrode serving as an anode and comprising a reversible, organic redox system located in said gas and test cell chamber, a cathode spaced from said anode and comprising an active mass having a redox potential higher than the redox potential of said anode, an immobilized electrolyte between said anode and said cathode, means connected between said anode and said cathode for measuring the short-circuit current therebetween; said diffusion electrode as the redox system comprising tetrachlor-p-benzoquinone or tetramethyl-p-benzoquinone.

* * * * *